United States Patent
Lamerichs et al.

(10) Patent No.: US 8,463,358 B2
(45) Date of Patent: Jun. 11, 2013

(54) ELIMINATION OF CONTRAST AGENT CONCENTRATION DEPENDENCY IN MRI

(75) Inventors: Rudolf Mathias Johannes Nicolaas Lamerichs, Eindhoven (NL); Rene Theodorus Wegh, Eindhoven (NL); Jeroen Alphons Pikkemaat, Eindhoven (NL); Holger Gruell, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 1043 days.

(21) Appl. No.: 12/303,453

(22) PCT Filed: Jun. 8, 2007

(86) PCT No.: PCT/IB2007/052179
§ 371 (c)(1),
(2), (4) Date: Dec. 4, 2008

(87) PCT Pub. No.: WO2007/141767
PCT Pub. Date: Dec. 13, 2007

(65) Prior Publication Data
US 2009/0196830 A1    Aug. 6, 2009

(30) Foreign Application Priority Data
Jun. 9, 2006  (EP) .................................. 06115211

(51) Int. Cl.
*A61B 5/05*    (2006.01)
(52) U.S. Cl.
USPC ............ 600/420; 600/407; 600/410; 600/419
(58) Field of Classification Search
None
See application file for complete search history.

(56) References Cited

U.S. PATENT DOCUMENTS

| | | | |
|---|---|---|---|
| 6,596,258 | B1 | 7/2003 | Ballesteros Garcia et al. |
| 6,676,963 | B1 | 1/2004 | Lanza et al. |
| 6,963,769 | B1 | 11/2005 | Balaban et al. |
| 2003/0129579 | A1 | 7/2003 | Bornhop et al. |
| 2003/0215392 | A1 | 11/2003 | Lanza et al. |
| 2003/0232012 | A1 | 12/2003 | Platzek et al. |
| 2005/0191243 | A1 | 9/2005 | Aime et al. |

FOREIGN PATENT DOCUMENTS

| | | |
|---|---|---|
| EP | 1331012 A1 | 7/2003 |
| EP | 1555539 A2 | 7/2005 |
| WO | 0066180 A2 | 11/2000 |
| WO | 2005122891 A1 | 12/2005 |
| WO | 2006032705 A2 | 3/2006 |
| WO | 2006114739 A2 | 11/2006 |

OTHER PUBLICATIONS

Kendrick R D, et al: "High-power H-19F excitation in a multiple-resonance single-coil circuit" Journal of Magnetic Resonance, vol. 75, No. 3, Dec. 1987, pp. 506-508, XP002429668.
Arne Hengerer, et al: Molecular magnetic resonance imaging, Biomedical Imaging and Intervention Journal 2006; 2(2):e8, pp. 1-7.
Arne Hengerer, et al: Molecular Magnetic Resonance Imaging, Siemens AG Medical Solutions, Sep. 2005.

*Primary Examiner* — Long V. Le
*Assistant Examiner* — Nicholas Evoy

(57) ABSTRACT

A method for MRI imaging to obtain information about a local physiochemical parameter after administration to a patient of a contrast agent including at least one non-responsive contrast enhancing entity that does not occur naturally in a human body and at least one responsive contrast enhancing entity attached to or mixed with the non-responsive contrast enhancing entity. By using such non-responsive contrast enhancing entities, a value for the physicochemical parameter can be obtained by acquiring only three images, providing a method which will be easier to apply in a clinical routine, since it will be faster and less sensitive to motion or flow artifacts.

22 Claims, 3 Drawing Sheets

ELIMINATION OF CONTRAST AGENT CONCENTRATION DEPENDENCY IN MRI

Figure 1:
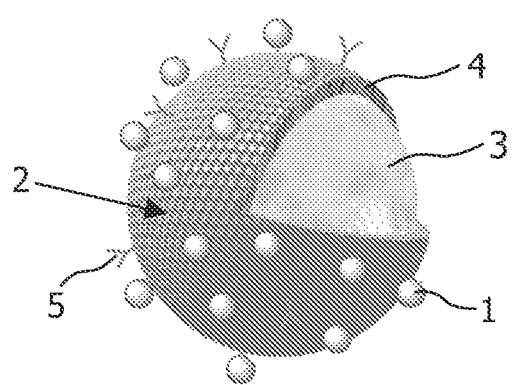

The present invention relates to Magnetic Resonance Imaging (MRI). More particularly, the present invention relates to a method for gaining information about a physicochemical parameter in at least a part of a body of an individual, e.g. by imaging using an agent sensitive to the physicochemical parameter, thereby eliminating contrast agent concentration dependency.

Magnetic Resonance Imaging (MRI) is one of the major diagnostic imaging techniques used in medicine. MRI generates detailed images of soft tissues. In MRI, specific properties of the various compounds found inside the tissues are used to generate the images, for this purpose, water present in the body is most commonly used. When subjected to a strong external magnetic field, the hydrogen atoms (protons) will align with this external field, resulting in a net magnetic moment. After excitation by an RF pulse, this magnetization will generate an RF signal that can be detected. This RF signal is characterized by a frequency that is related to the magnetic field strength. Therefore, magnetic field gradients are used to encode the spatial information, which is needed to reconstruct an image from the detected signals.

The relaxation times of the water signal are slightly different between different tissues. These differences are used to generate contrast in the images. In addition, the contrast can be manipulated by using contrast agents. Some contrast agents possess permanent magnetic dipoles, which influence the relaxation process of the nearby water protons and so lead to a local change of the image contrast. Other agents contain nuclei of a species that do not naturally occur in the human body, e.g. fluorine. In this case the signal will solely come from the added agent.

Another method to increase the clinical information of the images is by modulating the signal intensity by modifying the number of protons that actually contribute to the magnetization. A method to achieve this is by using Chemical Exchange Saturation Transfer (CEST), as described by Balaban et al. With the CEST technique additional differences in image contrast are obtained by altering the intensity of the water signal rather than differences in relaxation times $T_1$, $T_2$. This is done by selectively saturating the magnetization of a pool of exchangeable protons of a CEST contrast agent using an RF pulse. These protons subsequently transfer the saturation to nearby water by exchange with water protons, thereby decreasing the water signal. The extent of the water signal decrease depends on the proton exchange rate and on the concentration of the exchangeable protons. Since the proton exchange rate can depend on a local physicochemical parameter such as pH, this method enables pH mapping. This can yield important additional clinical information, e.g. detection of small tumors.

A disadvantage of pH mapping techniques using MRI and a contrast agent sensitive to the physicochemical parameter to be mapped, for example CEST, is that the signal that is obtained is not only dependent on the physicochemical parameter such as pH but also on the contrast agent concentration. Therefore, it is preferable that the most exact local concentration of the CEST agent is known, in order to determine the pH more exactly.

It is known that in pH mapping using the CEST technique, the dependency of the concentration of the contrast agent can be eliminated with a single CEST contrast agent having two exchangeable-proton pools, pool 1 and pool 2. These proton pools pool 1 and pool 2 have different resonance frequencies so that they can be saturated separately, and a different dependence of proton exchange on pH. By sequentially acquiring images using pre-saturation pulses at on-resonance and symmetrical off-resonance frequencies for both pool 1 and pool 2, the concentration dependence can be eliminated.

The fact that the above-described method of elimination of the dependency on the CEST contrast agent concentration needs two different exchangeable proton pools has some disadvantages. Selecting a single CEST agent, or a mixture of two CEST agents, presenting two suitable exchangeable proton pools with different pH dependencies of the proton exchange can be difficult in practice because the number of types of exchangeable entities suitable for CEST is limited. Most used exchangeable entities are amide protons and bound water. Moreover, the difference in pH dependence must be in the range that is clinically relevant for the desired application, preferably between pH 6.5 and pH 7.5.

Furthermore, in the case of two separate CEST agents, equal bio-distribution of the two molecules has to be assumed. Finally, to have two different exchangeable proton pools will always lead to a non-optimized maximum CEST effect because of a non-maximum concentration of exchangeable protons, since they have to be divided over the two pools.

A second way of eliminating the concentration dependency of the contrast agent is by using two saturation frequencies on one exchangeable-proton pool, as described in non-published co-pending international application with application number PCT/IB2006/051237 included herein by reference in its totality. In this method use is made of the shift of the resonance frequency of the exchangeable protons with changing exchange rate and therefore with changing pH. Two pre-saturation frequencies are chosen such that the CEST effects obtained at those frequencies have a very different dependence on pH. By sequentially acquiring images using pre-saturation pulses at these two on-resonance and the symmetrical off-resonance frequencies, the concentration dependence can be eliminated.

A disadvantage of the second method is that a compromise has to be made in saturation efficiency in order to obtain sufficiently different pH dependencies at two different saturation frequencies. If a too high saturation pulse power is used, then strong saturation can occur for both of the frequencies over a range of pH values. This means that the saturation pulse power cannot be too high, otherwise the saturation efficiency at the two chosen frequencies would be almost equal and less dependent on pH and hence indistinguishable. A consequence of a less than maximum saturation efficiency can be a less than maximum CEST effect, and therefore a higher concentration of CEST contrast agent will be needed to be detectable.

A further disadvantage of both methods described above is that four images have to be acquired and extensive data processing is needed.

Another disadvantage is that they are both only applicable to pH mapping using CEST.

Another method for the elimination of the concentration dependency of a parameter to be determined, which has been applied for pH mapping using an MRI contrast agent with a pH-dependent relaxivity, is successive injection of another contrast agent with pH-independent relaxivity. By assuming that the contrast agents have the same pharmacokinetics, it can be assumed that the local concentration and the evolvement over time of the concentration will be the same.

A disadvantage of this method is the need for two injections.

A further disadvantage is the need for assuming that both contrast agents will have the same pharmacokinetics, while this can be different since the contrast agents are different, and this can change over time due to changes in the tissue.

It is an object of the present invention to provide an alternative and preferably an improved method for providing an MRI image of at least a part of a body of a patient thereby reducing or eliminating contrast agent concentration dependency. The above objective is accomplished by a method according to the present invention.

In a first aspect of the present invention, a method for obtaining information concerning a physicochemical parameter by MRI imaging after administration to a patient of a contrast agent is provided. According to the present invention, the contrast agent comprises at least one non-responsive contrast enhancing entity giving a first signal, and at least one responsive contrast enhancing entity giving a second signal, the first signal being distinguishable from the second signal. The method comprises:

acquiring MR images of at least a part of a body of a patient comprising the at least one responsive contrast enhancing entity, acquiring a calibration image by recording the first signal from the non-responsive contrast enhancing entity, and determining a value of the physicochemical parameter from the MR images and the calibration image, whereby the calibration image is used to compensate the value of the physicochemical parameter for the dependence of the MR images on the concentration of the contrast agent.

Using non-responsive contrast enhancing for determining the concentration of the contrast agent has several advantages. The intensity of the excitation signal is independent of environmental properties such as, for example, pH or the presence of other substances or metabolites, or any other parameter which can be determined by use of MRI, for example $pO_2$.

Furthermore, since the total excitation signal only comes from the non-responsive contrast enhancing entity interpretation of the excitation image is unambiguous.

A main advantage of the method according to the present invention is that fewer images have to be combined in order to generate, for example, a concentration-independent pH map. As a consequence, the signal-to-noise ratio (SNR) of the pH map as determined by the method according to the present invention is improved with respect to prior art methods.

According to embodiments of the invention, MR imaging of one responsive contrast enhancing entity may be combined with nuclear radiation imaging of a non-responsive contrast enhancing entity including a radioactive substance. According to embodiments of the invention, the means for acquiring the MR images may use pre-saturation pulses.

According to preferred embodiments, MRI imaging may be used for both entities. An advantage of using MRI for both the responsive and non-responsive contrast enhancing entities is that it can be done simultaneously in a same apparatus.

According to embodiments of the invention, the method may furthermore comprise acquiring a spectrum of the non-responsive contrast enhancing entity, e.g. $^{19}F$ compound. The spectral data acquisitions can provide the concentration with a higher accuracy than the imaging methods.

According to other embodiments of the present invention, the first and second signal may have intensities and the method may furthermore comprise determining the ratio of first signal intensities used to generate the MR images and the intensity of the second signal used to generate the calibration image and deriving from this ratio the value of the physicochemical parameter.

According to embodiments of the present invention, the contrast agent may comprise a dual or multi-mode contrast agent. The contrast agent may include a non-responsive contrast enhancing entity with at least one responsive contrast enhancing entity. The contrast agent ma include the non-responsive contrast enhancing entity with attached thereto or linked thereto the at least one responsive contrast enhancing entity.

According to some embodiments, the at least one responsive contrast enhancing entity may covalently be bound to the non-responsive contrast enhancing entity, hereby forming one molecule. According to other embodiments of the present invention, the contrast agent may comprise a mixture of at least one non-responsive contrast enhancing entity and at least one responsive contrast enhancing entity without them being attached to each other.

According to embodiments of the present invention, the at least one non-responsive contrast enhancing entity may preferably have a MR resonance frequency significantly different from the proton-resonance frequency of water. The non-responsive contrast enhancing entity may comprise a proton nucleus with a resonance frequency significantly different from the resonance frequency of water. Most preferably the at least one non-responsive contrast enhancing entity does not occur naturally in a human body.

According to embodiments of the invention, the non-responsive contrast enhancing entity may comprise a non-native MRI-active nucleus, i.e. a nucleus which does not naturally occur in a human body and which is suitable for being used with MRI.

According to embodiments of the invention, the non-responsive contrast enhancing entity may have a gyromagnetic ratio close to the gyromagnetic ratio of hydrogen. The gyromagnetic ratio of hydrogen is 42.6 MHz/Tesla. Preferably, the non-responsive contrast enhancing entity may be a fluorine containing compound, which has a gyromagnetic ratio of 40.08 MHz/Tesla. The fluorine containing compound may, for example, comprise a perfluorocarbon core and a lipid shell or may comprise a polymer shell filled with a perfluorocompound. According to embodiments of the present invention, the non-responsive contrast enhancing entity may comprise a polymer shell filled with a compound or mixture of compounds that have proton resonance frequencies significantly different from the resonance frequency of water.

According to embodiments of the invention, the calibration image may be acquired by MRI or MRS.

According to preferred embodiment of the invention, the at least one responsive contrast enhancing entity may be a CEST contrast agent molecule. In the case a CEST contrast agent is used as the responsive contrast enhancing entity, the step of acquiring MR images may include:

acquiring a reference MRI image of at least a part of a body of a patient comprising the at least one CEST contrast agent molecule, acquiring a contrast enhanced MRI image of at least the part of the body of the patient comprising the at least one CEST contrast agent molecule, and determining the CEST effect in the part of the body from a comparison between the contrast enhanced MRI image and the reference MRI image.

Acquiring a reference MRI image of at least a part of a body of a patient may be performed by irradiation of the CEST contrast agent molecule at symmetrical off-resonance frequency and wherein acquiring a contrast enhanced MRI image of at least the part of the body of the patient is performed by irradiation at exchangeable proton frequency of the CEST contrast agent molecule.

According to embodiments of the present invention, the CEST contrast agent molecule may comprise at least one CEST-active paramagnetic complex, the at least one CEST-active paramagnetic complex comprising at least one exchangeable entity for enabling CEST. The paramagnetic complex may, for example, be a Yb-DOTAM derivative.

In the specific example of the responsive contrast enhancing entity being a CEST contrast agent molecule, the physicochemical parameter may be determined by determining the ratio of $(M_0^* - M_s)/M_s)$ AND $M_F(0)$ and deriving from this ratio the physicochemical parameter.

According to preferred embodiments of the present invention, the physicochemical parameter may be pH. However, also other physicochemical parameters such as, for example, temperature, $pO_2$ or metabolite concentration may be determined by using the method according to the present invention.

The present invention also discloses a computer program product which, when executed on a processing device, performs or controls the method according to the present invention, and a machine-readable data storage device storing the computer program product according to the present invention.

In a second aspect of the present invention, a system for MR imaging is provided. According to the invention, the system is for use with a contrast agent comprising at least one non-responsive contrast enhancing entity giving a first signal and at least one responsive contrast enhancing entity giving a second signal, the first signal being distinguishable from the second signal. The system comprises:

means for acquiring MR images of at least a part of a body of a patient comprising the at least one responsive contrast enhancing agent, means for acquiring a calibration image of the part of the body of a patient by recording the first signal from the at least one non-responsive contrast enhancing entity, and means for determining a value for a physicochemical parameter in the part of the body by reducing or eliminating the effect on the physicochemical parameter of concentration dependency of the contrast agent using the calibration image.

According to embodiments of the invention, the means for acquiring the MR images may use pre-saturation pulses.

According to embodiments, the system may comprise a first coil suitable for exciting the responsive contrast enhancing entity, e.g. CEST contrast agent, and a second coil suitable for exciting the non-responsive contrast enhancing entity, e.g. the fluorine compound.

In a third aspect of the present invention, a contrast agent is provided. The contrast agent may comprise a dual or multimode contrast agent. The contrast agent comprises at least one non-responsive contrast enhancing entity and at least one responsive contrast enhancing entity. Non-responsive contrast enhancing entities may be suitable contrast enhancing entities for use in diagnostic imaging methods such as e.g. optical methods, e.g. fluorescence imaging or near-infrared diffuse optical tomography (DOT), X-ray, PET, MRI, ultrasound or CT scan or modifications or derivatives of these. Responsive contrast enhancing entities may be suitable contrast enhancing entities for use in diagnostic methods where the contrast achieved depends upon the concentration or level of the physical parameter in the environment of the contrast agent such as e.g. MRI, especially CEST MRI.

Using contrast agents comprising non-responsive contrast enhancing entities for determining the concentration of the contrast agent has several advantages. By using such a contrast agent the intensity of the excitation signal is independent of environmental properties such as, for example, pH or the presence of other substances or metabolites, or any other parameter which can be determined by use of MRI, for example $pO_2$.

Furthermore, since the total excitation signal only comes from the non-responsive contrast enhancing entity interpretation of the excitation image is unambiguous.

Optionally, the present application claims contrast agents excluding ones restricted to a carrier having a plurality of different paramagnetic CEST-active complexes linked thereto such as two different CEST-active complexes and no other types of contrast enhancing agent or in which none of the contrast agents are responsive, or excluding ones restricted to mixtures of different CEST-active complexes, e.g. different paramagnetic CEST-active complexes. Optionally, the present application claims contrast agents excluding the ones that comprise mixtures of two or more contrast enhancing agents in which none of the contrast agents are responsive. Optionally, the present application claims contrast agents excluding any agents disclosed in PCT/IB2006/051237.

A main advantage of the contrast agent according to the present invention is that it allows to use fewer images to be combined in order to generate, for example, a concentration-independent pH map. As a consequence, the signal-to-noise ratio (SNR) of e.g. the pH map as determined by the method according to the present invention is improved with respect to prior art methods.

According to embodiments of the present invention, the non-responsive contrast enhancing entity may have a MR resonance frequency significantly different from the proton-resonance frequency of water. The non-responsive contrast enhancing entity may comprise a proton nucleus with a resonance frequency significantly different from the resonance frequency of water. Preferably, the non-responsive contrast enhancing entity does not occur naturally in a human body.

According to embodiments of the invention, the non-responsive contrast enhancing entity may have a gyromagnetic ratio close to the gyromagnetic ratio of hydrogen. The gyromagnetic ratio of hydrogen is 42.6 MHz/Tesla. Preferably, the non-responsive contrast enhancing entity may be a fluorine containing compound, which has a gyromagnetic ratio of 40.08 MHz/Tesla. The fluorine containing compound may, for example, comprise a perfluorocarbon core and a lipid shell or may comprise a polymer shell filled with a perfluoro-compound. According to embodiments of the present invention, the non-responsive contrast enhancing entity may comprise a polymer shell filled with a compound or mixture of compounds that have proton resonance frequencies significantly different from the resonance frequency of water.

The contrast agent may comprise the non-responsive contrast enhancing entity with attached thereto the at least one responsive contrast enhancing entity. According to embodiments of the present invention, the at least one responsive contrast enhancing entity may covalently be bound to the non-responsive contrast enhancing entity, hereby forming one molecule. According to other embodiments of the present invention, the contrast agent may comprise a mixture of at least one non-responsive contrast enhancing entity and at least one responsive contrast enhancing entity without them being attached to each other.

According to preferred embodiments of the present invention, the responsive contrast enhancing entity may comprise a CEST contrast agent molecule. The CEST contrast agent molecule may comprise at least one CEST-active paramagnetic complex, the at least one CEST-active paramagnetic complex comprising at least one exchangeable entity for enabling CEST. The paramagnetic complex may be a Yb-DOTAM derivative.

In a further aspect of the present invention, an IV preparation comprising the contrast agent according to the present invention is provided for being administrated directly into the veins of the patient.

Particular and preferred aspects of the invention are set out in the accompanying independent and dependent claims. Features from the dependent claims may be combined with features of the independent claims and with features of other dependent claims as appropriate and not merely as explicitly set out in the claims.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

Figure 2:
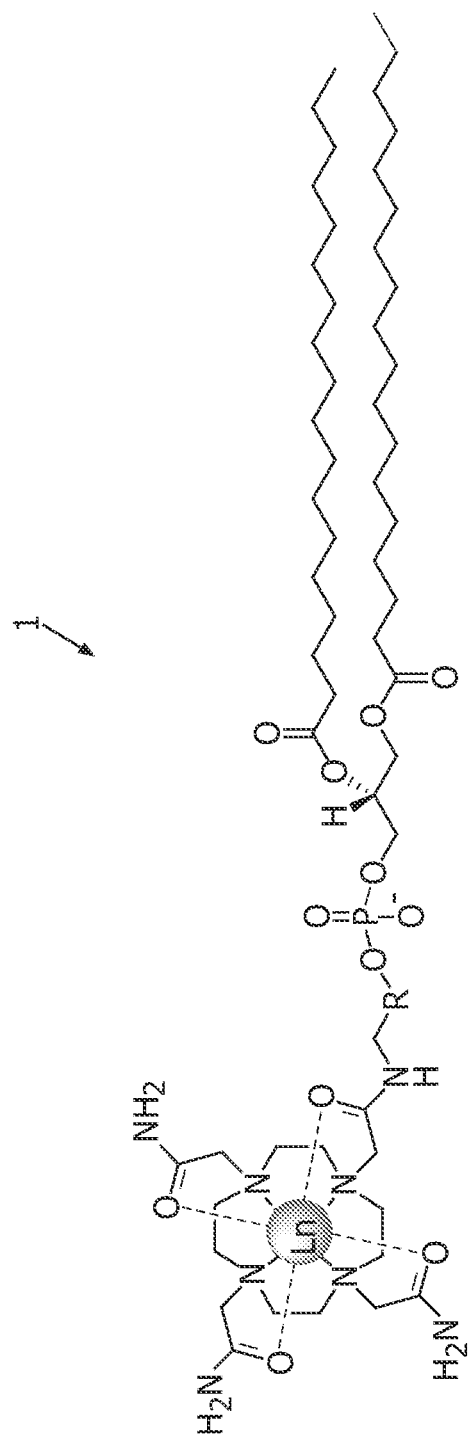
Figure 3:
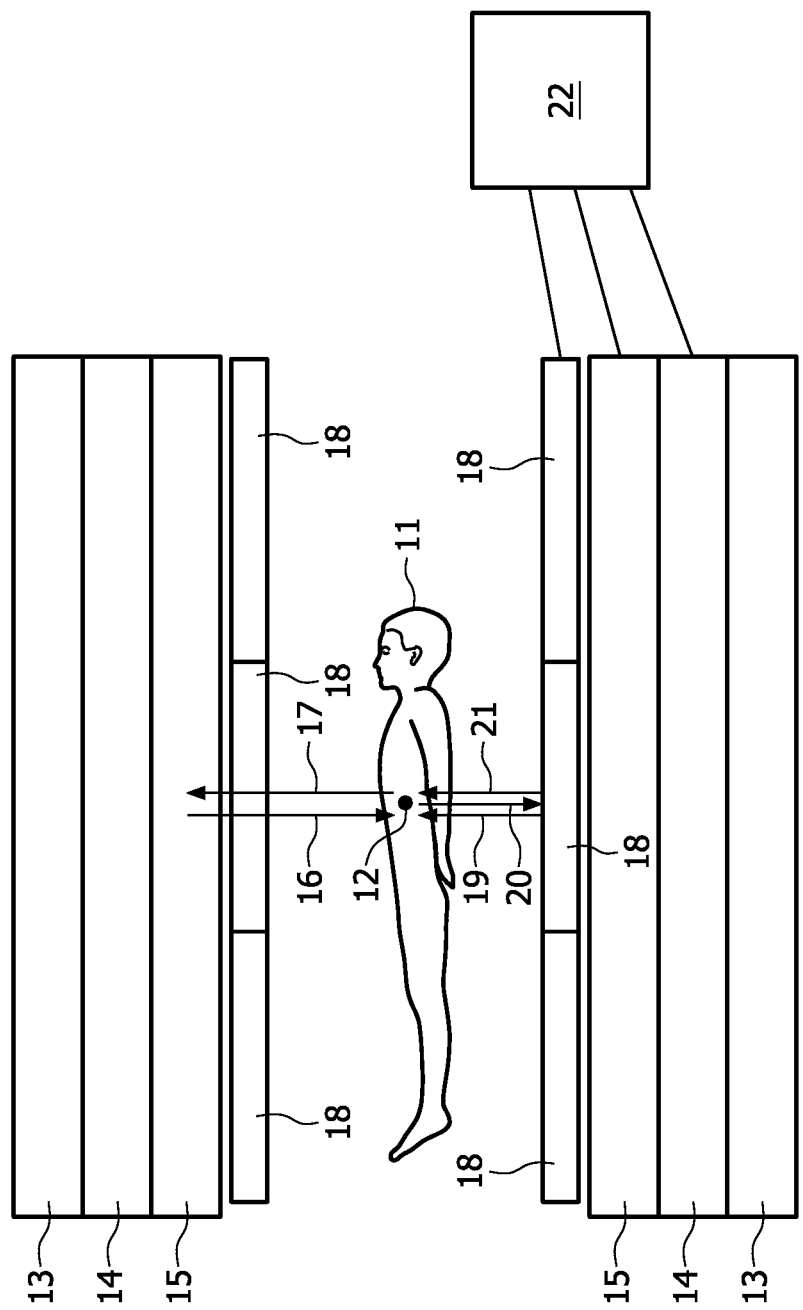

FIG. 1 illustrates a contrast agent according to an embodiment of the present invention, FIG. 2 shows an example of a responsive contrast enhancing entity which may be used according to embodiments of the present invention, FIG. 3 shows a schematic representation of a system according to an embodiment of the present invention.

In the different figures, the same reference signs refer to the same or analogous elements.

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof.

The following terms are provided solely to aid in the understanding of the invention. These definitions should not be construed to have a scope less than understood by a person of ordinary skill in the art.

Contrast Agent (CA):
a chemical substance which is introduced into an organism to change the contrast between two tissues when imaged.

Contrast Agent Unit:
specific example of the contrast agent according to the present invention, in which the contrast agent comprises at least one non-responsive contrast enhancing entity and at least one responsive contrast enhancing entity attached to, associated with or mixed with this non-responsive contrast entity.

Non-Responsive Contrast Enhancing Entity:
molecule or compound with a response or a contrast enhancing ability that is independent of the physicochemical parameter to be determined. The response of the non-responsive enhancing entity depends on the concentration of that entity.

Responsive Contrast Enhancing Entity:
molecule or compound with a response or a contrast enhancing ability that is dependent on the physicochemical parameter to be determined. For these entities, the response depends on both the concentration of the entity and an external trigger, e.g. RF irradiation in the case of CEST.

Non-Native Signal:
signal solely coming from one entity, according to an aspect of the present invention, a signal, for example, solely coming from the non-responsive contrast enhancing entity.

Chemical Exchange Saturation Transfer (CEST):
refers to all saturation transfer processes that are dependent on chemical exchange between two molecules which exhibit different magnetic resonance frequencies.

CEST Effect:
extent of the decrease of the signal used to generate the MR image, caused by CEST, e.g. the water proton signal decrease in the case of proton imaging. The CEST effect can be written as $1-M_S/M_0^*$, wherein $M_S$ is the intensity of that signal upon pre-saturation of the exchangeable entities, e.g. exchangeable protons, and $M_0^*$ is the intensity of that signal upon irradiating at an off-resonance frequency, preferably at the opposite side of the frequency spectrum relative to that signal (symmetrical off-resonance).

CEST Contrast Agent (CA):
material having at least one exchangeable entity, e.g. proton, that can chemically exchange for exchangeable entities, e.g. protons, of another material, and which can be used to perform CEST imaging. The exchangeable entity, e.g. proton, may or may not be incorporated in an exchangeable molecule or group of atoms, e.g. a water molecule.

Water Proton Signal:
The signal in the proton NMR spectrum caused by the resonance of the protons of free water, the signal having a frequency and an intensity.

Magnetic Resonance Imaging (MRI):
Imaging technique where nuclear magnetic resonance is used to construct an image of a subject in order to obtain medical information.

Resonance Frequency:
Frequency at which a component of a molecule or atom resonates, e.g. at which a nuclear spin resonates.

The present invention relates to methods and systems for gaining information about a human or animal patient, and especially to methods of diagnosis based on magnetic resonance imaging (MRI). By way of introduction to the present invention, the result of MRI measurements, i.e. an MRI signal, when the aim is measuring a physicochemical parameter, usually depends on the parameter to be measured as well as on the concentration of the contrast agent used to obtain the MRI signal. For example, in pH mapping, the MRI signal depends on the pH but also on the concentration of the contrast agent used in order to obtain the MRI signal.

The present invention provides a method for reducing or eliminating the contrast agent concentration dependency in Magnetic Resonance Imaging (MRI). In a preferred aspect of the present invention reducing or eliminating the contrast agent concentration dependency is part of 'smart imaging' or 'imaging with a responsive entity" (see further), i.e. for determining a value for a physicochemical parameter local to the contrast agent.

The method according to the present invention makes use of a contrast agent unit comprising at least one first contrast enhancing entity and at least one second contrast enhancing entity attached to, or associated with or mixed with the first contrast enhancing entity. According to the present invention, the at least one first contrast enhancing entity is a non-responsive entity, i.e. an entity having, e.g. upon irradiation or of its own nature, a response or a contrast enhancing ability that is independent of the physicochemical parameter to be determined. The non-responsive contrast enhancing entity can be, for example, a fluorine containing compound. The non-responsive contrast enhancing entity can be one suitable for use in diagnostic imaging methods such as e.g. optical methods, e.g. fluorescence imaging or near-infrared diffuse optical tomography (DOT), X-ray, PET, MRI, ultrasound or CT scan or modifications or derivatives of these. An example of a contrast enhancing agent for DOT is indocyanine green (ICG). An example of a contrast enhancing agent for PET is a radionuclide.

The second contrast enhancing entity is a responsive entity, i.e. an entity having, e.g. upon irradiation, a response or a contrast enhancing ability that is dependent on the physicochemical parameter to be determined. The second contrast enhancing entity can be, for example, a CEST-active molecule.

The present invention is applicable to the determination of other or more physicochemical parameters than pH, e.g. also to temperature, metabolite concentration, and other methods than CEST, e.g. pH-dependent relaxivity.

According to the present invention, the at least one first non-responsive contrast enhancing entity is an entity that does not naturally occur within a human or animal body (i.e. is non-native with respect to the human or animal body) and preferably has a MR resonance frequency significantly different from the proton-resonance frequency of water. According to embodiments of the present invention, the non-responsive contrast enhancing entity may comprise a proton nucleus with a resonance frequency significantly different from the resonance frequency of water.

According to specific embodiments of the invention, a contrast agent unit is provided comprising a first non-responsive contrast enhancing entity with attached thereto, or associated therewith or mixed therewith at least one second, responsive contrast enhancing entity, which responsive contrast enhancing entity is suitable to be used with MRI. According to preferred embodiments, a contrast agent may comprise more than one second, responsive contrast enhancing entity attached to the first, non-responsive contrast enhancing entity. However, in other embodiments, the contrast agent may comprise only one second, responsive contrast enhancing entity. Preferably, it should be assured that enough contrast agent is present at the region of interest for the method to be reliable, i.e. in order to obtain a reliable signal.

Where the at least one second, responsive contrast enhancing entity is attached to, associated with or mixed with the first, non-responsive contrast enhancing entity, compounds that may be used for the first, non-responsive contrast enhancing entity according to the present invention include compounds which have a suitable gyromagnetic ratio and which, as already said, do not naturally occur in a human body and have a MR resonance frequency significantly different from the proton-resonance frequency of water. The gyromagnetic ratio of atomic nuclei plays a central role in MRI. The ratio, which is different for every nucleus, indicates the frequency with which a nucleus will precess around an externally applied magnetic field. Non-responsive contrast enhancing entity compounds suitable to be used with the present invention may preferably have a gyromagnetic ratio close to the gyromagnetic ratio of hydrogen, which is 42.6 MHz/Tesla The higher the gyromagnetic ratio of an atomic nucleus is, the higher the effect will be upon irradiating the atomic nucleus with a frequency suitable for exciting the atomic nucleus, and thus the better it is for being used with the method according to embodiments of the present invention. It is known that hydrogen has the highest gyromagnetic ratio of all MR detectable nuclei, and that fluorine has the second highest gyromagnetic ratio with a value of 40.08 MHz/Tesla. Therefore, and because fluorine does not occur naturally in the human body, fluorine containing compounds are good candidates to be used with embodiments of the method according to the present invention. Because of that, the method according to the present invention will be further discussed by means of fluorine containing compounds. However, it has to be understood that this is not limiting the invention in any way and that other suitable non-responsive contrast enhancing entity compounds with properties as described above, e.g. with a suitable gyromagnetic ratio and which do not naturally occur in the body, may also be applied with the method according to the present invention.

In a specific example of the above described embodiments, the at least one second, responsive contrast enhancing entity may be covalently bond to the first, non-responsive contrast entity, hereby forming one molecule.

According to other embodiments of the present invention, the contrast agent may comprise a mixture of the first, non-responsive contrast enhancing entity and the second, responsive contrast enhancing entity without them being attached to each other.

In embodiments according to the present invention, MR imaging may be combined with other imaging techniques, such as PET, nuclear imaging, optical imaging such as near-infrared diffuse optical tomography (DOT), X-ray, ultrasound or CT scan or modifications or derivatives of these. In at least some of these cases the first, non-responsive contrast enhancing entity may be irradiated using the same or another technique than for irradiation of the second, responsive contrast enhancing entity. The irradiation may be, for example, ultrasound radiation, and the first contrast enhancing entity may be an ultrasound contrast agent. Alternatively, the first, non-responsive contrast enhancing entity may deliver a signal inherent to itself which can be used for imaging. An example of such a contrast entity is one comprising a radioactive material. A radioactive material can provide a signal which provides an image with good contrast with respect to the background radioactivity of the human body. An example of a combined PET and MRI apparatus is described in "Molecular magnetic resonance imaging", by Hengerer and Grimm, Biomedical Imaging and intervention Journal, 2006; 2(2):e8.

Accordingly, one embodiment possibility is to combine MR imaging of one responsive contrast enhancing entity with nuclear radiation imaging of a non-responsive contrast enhancing entity including a radioactive substance. An example of a contrast agent which may be used for these purposes may, for example, comprise CEST metal complexes, that represent the responsive contrast enhancing entity, mixed with or attached to a small amount of similar radioactive metal complexes that will form the non-responsive contrast enhancing entity. For example, for a combination of MR imaging with nuclear imaging, Yb-DOTAM derivatives may be used for the second, responsive contrast enhancing entity together with a small fraction (e.g. $\frac{1}{1000}$) of DOTAM complexed with a radioactive metal complex which can be used for the first, non-responsive contrast enhancing entity. An advantage of this is that small particles can be used, which is important for smart imaging.

However, another possibility is the use of large particles which incorporate a well defined amount of responsive contrast enhancing entities and nuclear imaging entities, i.e. non-responsive contrast enhancing entities. An advantage of this is that the ratio between the non-responsive and responsive contrast enhancing entities is better defined. For example, liposomes or emulsion particles with Yb-DOTAM lipids and $^{99}$Tc-DOTA(M) lipids can be used for this purpose.

Hereinafter, the invention will be mainly described with respect to MR imaging for both entities as an example of the present invention only. An advantage of using MRI for both the responsive and non-responsive contrast enhancing entities is that it can be done simultaneously in a same apparatus. Also, the present invention will further be described by means of contrast agents comprising a first non-responsive contrast enhancing entity with attached thereto at least one second, responsive contrast enhancing entity. It has to be understood that this does not limit the invention in any way and that other contrast agents comprising other suitable first, non-responsive and second, responsive contrast enhancing entities or contrast agents comprising a mixture of first, non-responsive and second, responsive contrast enhancing entities, also may be used according to the present invention. Furthermore, the invention will be described by means of an example of pH mapping, i.e. the physicochemical parameter is pH. It has to be understood that the invention can also be applied for other physicochemical parameters, such as temperature, metabolite concentration, the presence of other substances or metabolites, or any other parameter which can be determined by use of MRI, such as for example $pO_2$.

A method according to the present invention comprises, in a first step, administrating to a human body of a patient a contrast agent comprising at least one first, non-responsive contrast enhancing entity and at least one second contrast enhancing entity. In the example given, the contrast agent comprises one non-responsive contrast enhancing entity with attached thereto at least one responsive contrast enhancing entity suitable for MRI. As already described above, the first, non-responsive contrast enhancing entity may preferably be a fluorine containing compound which has attached thereto in a suitable way at least one responsive contrast enhancing entity, the responsive contrast enhancing entity being suitable for being used in MRI.

By irradiating the non-responsive contrast enhancing entity, e.g. fluorine containing compound, with electromagnetic radiation at a suitable frequency, i.e. at a frequency suitable for exciting the non-responsive contrast enhancing entity, the non-responsive contrast enhancing entity, e.g. fluorine containing compound, generates an excitation signal, in case of a fluorine compound a fluorine or $^{19}$F signal.

Because the non-responsive contrast enhancing entity, e.g. fluorine containing compound, does not naturally occur in the human body, it can be safely assumed that the excitation signal, e.g. fluorine or $^{19}$F signal, will solely come from this non-responsive contrast enhancing entity, e.g. fluorine containing compound, and therefore will be a direct measure for the concentration of the non-responsive contrast enhancing entity, e.g. fluorine containing compound. Because one knows how many responsive contrast enhancing entities are attached to the non-responsive contrast enhancing entity, e.g. fluorine containing compound, the excitation signal, e.g. fluorine or $^{19}$F signal, will also be a direct measure for the concentration of the responsive contrast enhancing entity.

Using non-responsive contrast enhancing entities as described above, e.g. fluorine containing compounds, for determining the concentration of the contrast agent has several advantages. The intensity of the excitation signal, e.g. fluorine or $^{19}$F signal, is independent of environmental properties such as, for example, pH or the presence of other substances or metabolites, or any other parameter which can be determined by use of MRI, for example $pO_2$. The T1 and T2 effect (relaxation times), known in conventional MRI, in the signal intensity can be eliminated by acquiring non-responsive contrast enhancing entity density maps, e.g. fluorine density maps, which are similar to proton density maps as known in conventional MRI. Furthermore, since the total excitation signal, e.g. fluorine or $^{19}$F signal, only comes from the non-responsive contrast enhancing entity, e.g. fluorine containing compound, interpretation of the excitation image, e.g. fluorine or $^{19}$F images is unambiguous. In the further description, the excitation image will be referred to as calibration image, because this image is used to determine the concentration of the contrast agent, which then is used to eliminate the contrast agent concentration dependence of the parameter to be measured. Furthermore it is possible to acquire the spectrum of the $^{19}$F compound. The spectral data acquisitions can provide the concentration with a higher accuracy than the imaging methods. Also the imaging data may be enhanced with spectral information in order to identify the $^{19}$F compound more accurately.

According to a preferred embodiment of the present invention, the responsive contrast enhancing entity may be a Chemical Exchange Saturation Transfer or CEST contrast agent. Hereinafter, the method according to the present invention will be further described in detail for the case where the responsive contrast enhancing entity is a CEST contrast agent molecule. It has, however, to be understood that this is not limiting the invention in any way and that the method can also be applied with responsive contrast enhancing entities other than CEST contrast agent molecules. An example of an MRI method other than CEST which can be used according to the present invention may, for example, be pH-dependent relaxivity. According to this preferred embodiment, CEST may be used for, for example, pH mapping. By using the method according to the present invention, the concentration dependency of the CEST contrast agent molecules in pH mapping may be reduced or eliminated by using the signal from the non-responsive contrast enhancing entity as described above, e.g. fluorine containing compound. Hereinafter, the method according to the present invention will be described by using a fluorine containing compound, and more particularly a $^{19}$F fluorine containing compound. It has again to be understood that this does not limit the invention in any way and that other non-responsive contrast enhancing entities may be used according to embodiments of the present invention.

The method according to preferred embodiments of the invention in general relies on a specific construct in which responsive contrast enhancing entities, e.g. CEST contrast agent molecules, are attached to the non-responsive contrast enhancing entities, e.g. fluorine containing compound. This can be done in several ways. For example, the responsive contrast enhancing entities, e.g. CEST contrast agent molecules, may covalently be bound to the non-responsive contrast enhancing entity, e.g. fluorine containing compound, thereby incorporating the non-responsive contrast enhancing entity, e.g. fluorine, and the protons needed for MRI in one molecule. According to other embodiments, the contrast agent may comprise a mixture of non-responsive contrast enhancing entities and responsive contrast enhancing entities.

Hence, according to this preferred embodiments of the invention, at least one CEST contrast agent molecule may be attached to a non-responsive contrast enhancing entity, e.g. fluorine containing compound. This can be done by, for example, covalently incorporating the non-responsive contrast enhancing entity, e.g. fluorine, and the exchangeable protons needed for CEST in one molecule. However, in the specific example of a fluorine containing compound and in order to obtain a sufficient excitation signal, e.g. fluorine or $^{19}F$ signal, a construct as illustrated in FIG. 1 is more feasible in which there are several fluorine atoms. In this structure, responsive contrast enhancing entities 1, in the example given CEST contrast agent molecules are attached to a non-responsive contrast enhancing entity 2, e.g. a fluorine containing compound. In the example given, the fluorine containing compound may comprise a fluorine containing core 3 and a shell 4, which may be a lipid shell such as, for example, a phospholipid shell. Optionally, the lipid shell may be provided with target binding sites 5. An example of the binding sites 5 are antibodies.

According to embodiments of the present invention, the fluorine containing core 3 may, for example, be a perfluorocarbon core made of, for example, perfluoro-octylbromide (PFOB), perfluoro-crown ethers (PFCE), or other suitable perfluoro compounds. The fluorine containing compound 2 may be a fluorine containing particle. In the further description the fluorine containing compound 2 will be referred to as fluorine containing particle 2. The size of these fluorine containing particles 2 may generally be in the nanometer range and may preferably be between 50 and 500 nm. Again, it has to be understood that this is only by way of an example and that this also applies to other contrast entities.

According to other embodiments of the invention, the fluorine containing particles 2 may comprise a shell 4 made from polymers instead of phospholipids and this polymer shell 4 may be then be filled with, for example, a perfluoro compound. According to other embodiments of the invention, the polymer shell 4 may be filled with a compound or mixture of compounds that have proton resonance frequencies significantly different from the resonance frequency of water.

To be useful as CEST contrast agent, the polymer shell 4 should comprise exchangeable entities, for example exchangeable protons, or CEST-active molecules should be attached to the polymer shell 4. Hence, according to these embodiments of the present invention, the non-responsive contrast entity 2 is formed by the perfluoro compound and the responsive contrast enhancing entities 1, in the example given CEST contrast agent molecules, are comprised within or attached to the polymer shell. The polymer shell may be a biodegradable polymer shell, made from e.g. poly-(lactic-acid), poly-(glycolic-acid), poly-caprolacton, poly-(alkyl-cyanoacylates) and poly-(amino-acids) and copolymers thereof.

To the shell 4 of any of these fluorine containing particles 2, which may, as described above, have a size between 50 and 500 nm, in the example given about 10,000, responsive contrast enhancing entities 1, e.g. CEST contrast agent molecules, may then be attached in order to obtain a sufficient signal. In the case of a fluorine containing particle 2 comprising a lipid shell this can be done by adding the responsive contrast enhancing entities 1, e.g. CEST contrast agent molecules, such as, for example, illustrated in FIG. 2, to a lipid mixture that will form the shell 4. The lipids will stabilize the hydrophobic perfluoro-emulsion droplets in water by forming a monolayer around them, with the hydrophobic acyl chains pointing towards the perfluorocarbon core 3 and the polar head group directing towards the outside water phase. An example of a lipid mixture suitable for being used according to the invention may, for example, be a mixture of 60% lecithin, 20% cholesterol and 20% lipophilic CEST contrast agent molecules. It has to be understood that this is only an example and that mixtures having other compositions and/or other concentrations may also be used.

Since, according to a preferred embodiment of the invention, the CEST active part is covalently attached to the polar head group of a phospholipid, it will protrude from the shell 4 into the water phase enabling optimal proton exchange with water, which is necessary for performing CEST measurements.

FIG. 2 shows an example of a CEST contrast agent molecule 1 that may be used with the method according to the present invention. It has to be understood that other known CEST contrast agent molecules can also be used.

According to the present invention, any suitable CEST contrast agent molecule may be used. For example, a CEST-active paramagnetic complex may be used which may comprise a paramagnetic ion attached to a chelating ligand. The paramagnetic ion may for example be a lanthanide ion or any other paramagnetic ion such as a transition metal ion. The chelating ligand may be DOTAM or a DOTAM derivative (e.g. DOTAM with at every amide group one amide proton substituted by, for example, $COO^-$, $COOEt$, $PO_3^{2-}$, etc.). The paramagnetic complex may then, for example, be a Yb-DOTAM complex. The R-group in FIG. 2 can be, for example C, $(CH_2)_n CONHCH_2CH_2$, $CH_2(OCH_2CH_2)_n$, or $CH_2(OCH_2CH_2)_n CONHCH_2CH_2$.

In the case that, instead of CEST, for example a responsive contrast enhancing entity with a pH-dependent relaxivity is used to determine the pH, fluorine, as well as other suitable non-responsive contrast enhancing entities, can also be used to eliminate the concentration dependency caused by the responsive contrast agent. The construct can be very similar to the one described above, except that the responsive contrast enhancing entity in this case is a paramagnetic complex with a pH-dependent relaxivity which may be attached to a phospholipid. The paramagnetic ion may, for example, be Gd, and the chelating ligand may, for example, be DOTA4 Amp, or a derivative thereof.

The non-responsive contrast enhancing entity particles, e.g. fluorine containing particles 2 as illustrated in FIG. 1, may be characterized by a well defined size and therefore a well defined amount of non-responsive contrast enhancing entity, e.g. fluorine or $^{19}F$, and number of responsive contrast enhancing entities, in the example given CEST contrast agent molecules 1, attached to the non-responsive contrast enhancing entity particles, e.g. fluorine containing particle 2. The non-responsive contrast enhancing entity particles, e.g. fluorine containing particles 2, with the responsive contrast enhancing entities, in the example given CEST contrast agent molecules 1, attached thereto may be provided to a human body in the form of, for example, an emulsion. To obtain a well defined size of the non-responsive contrast enhancing entity particles, e.g. fluorine containing particles 2, the emulsion may usually be processed in an emulsifier, i.e. emulsion streams are made to collide under very high pressure thereby altering the size of the emulsion droplets. Preferably, the non-responsive contrast enhancing entity particles, e.g. fluorine containing particles 2, may be present in the emulsion in a very low concentration, i.e. in the nano-molar ($10^{-9}$ M)

range or even in the pico-molar ($10^{-12}$ M) range. Depending on the size of the non-responsive contrast enhancing entity particles 2 the local concentration of fluorine compound at a particular position of interest in the body of a patient after administration of the emulsion can still be in the milli-molar ($10^{-3}$ M) range. This high content of non-responsive contrast entities 2, e.g. fluorine, present in the body of a patient after administration of the emulsion to the body allows for fast data acquisition. It has to be noted that the emulsions are very stable because of the fact that the perfluorocarbon compound does not dissolve in water.

The complete contrast agent may be provided in the form of an intravenous (IV) composition to be administrated to the body of a patient directly into the veins of that patient.

Quantification of the concentration of the non-responsive contrast enhancing entity 2, e.g. fluorine containing compound, can, in the example given, be performed either by MR imaging or MR spectroscopy of the excitation signal, e.g. fluorine or $^{19}$F signal, originating from the core 3 of the non-responsive contrast enhancing entity particles, e.g. fluorine containing particles 2. Since, according to the present invention, the non-responsive contrast enhancing entity 2, e.g. fluorine containing compound, does not naturally occur in the human body, the excitation signal coming from non-responsive contrast enhancing entities 2, in the case of a fluorine containing compound the fluorine or $^{19}$F signal, does not naturally occur in the body. Because of that, the excitation signal, e.g. fluorine or $^{19}$F signal, is a unique signature for the amount of non-responsive contrast enhancing entity particles, e.g. fluorine containing particles 2. From the excitation signal, e.g. fluorine or $^{19}$F signal, the concentration of the non-responsive contrast enhancing entity 2, e.g. fluorine containing compound, and in the specific case of FIG. 1 the perfluoro compound, can be determined. Both the dimensions of the non-responsive contrast enhancing entity particles, e.g. fluorine containing particles 2, and the number of responsive contrast enhancing entities 1, e.g. CEST contrast agent molecules, per particle 2 are well defined before performing an experiment or measurement, allowing the determination of the concentration of the responsive contrast enhancing entity 1, e.g. CEST contrast agent molecules. If this concentration is known, the actual pH can be derived, e.g. from the pH-dependent CEST effect.

In the specific case of the responsive contrast enhancing entity or contrast agent molecule 1 being a CEST contrast agent molecule, the measurement itself comprises, after providing the emulsion comprising the contrast agent, i.e. comprising non-responsive contrast enhancing entity particles, e.g. fluorine containing particles 2, with the CEST contrast agent molecules 1 attached thereto to the patient, a first step of determining the change in water proton signal intensity due to the presence of the CEST contrast agent molecules. This may be done by acquiring two different images, i.e. a first, so-called $^1$H image, which may be obtained by irradiation of the non-responsive contrast enhancing entity 2 with the responsive contrast enhancing entities, in the example given the CEST contrast agent molecules 1, attached thereto at a frequency corresponding with exchangeable amide proton frequency, and a second, so-called control or reference $^1$H image, which may be acquired by irradiating the non-responsive contrast enhancing entity 2 with the responsive contrast enhancing entities, in the example given the CEST contrast agent molecules 1, attached thereto at a symmetrical off-resonance frequency, generally known in MRI. The term "symmetrical" in this case means symmetrical with respect to the bulk water proton signal. The images are called $^1$H images because the signal that is measured is coming from protons.

The difference in signal intensity between the first $^1$H image and the second, control or reference $^1$H image is, in the example given, due to the CEST effect.

The amplitude of this difference depends on both the concentration of the contrast agent molecules 1, in the example given the concentration of the CEST contrast agent molecules, and on the parameter that is measured, in the preferred embodiment of the present invention the pH. In the example given, in order to get a correct pH map the concentration of the CEST contrast agent must be known. For this purpose a third, excitation signal image, e.g. fluorine or $^{19}$F image ($M_F$) may be acquired by irradiating the non-responsive contrast enhancing entity, e.g. fluorine containing compound, with attached thereto the responsive contrast enhancing entities, e.g. CEST contrast agent molecules 1, with radiation at a suitable frequency, the suitable frequency depending on the non-responsive contrast enhancing entity 2 used. For example, at a field-strength of 3 T, a suitable frequency for irradiating a fluorine containing compound according to embodiments of the present invention may be 122 MHz.

As already described above, in other embodiments according to the present invention other techniques can be used for obtaining a signal form the non-responsive contrast enhancing entity. For example, the non-responsive contrast enhancing entity may be irradiated by means of ultrasound or may be radiating itself, e.g. it provides a nuclear radiation (radioactivity) signal.

In the specific case of CEST contrast agent molecules 1 being the responsive contrast enhancing entity, the decrease of the water signal due to CEST may be described by:

$$\frac{M_s}{M_0^*} = \frac{1}{1 + k_{CA}[CA]n_{ex}T_{1W}} \quad (1)$$

wherein $M_S$ and $M_0^*$ are the water signal intensities for on-resonance and symmetrical off-resonance irradiation respectively, $k_{CA}$ is the single exchange site rate constant, [CA] is the contrast agent concentration, $n_{ex}$ is the total number of chemical exchange sites (normally exchangeable protons) per contrast agent unit, and $T_{1W}$ is the longitudinal relaxation time constant of the water protons. According to the present example of the present invention, a contrast agent is formed by a non-responsive contrast enhancing entity particle, e.g. a fluorine containing particle 2, e.g. containing one or more fluorine atoms, with at least one responsive contrast enhancing entity, in the specific example CEST contrast agent molecule 1, attached thereto. This relation follows from the modified Bloch equations and is valid under the condition that the exchangeable protons of the CEST contrast agent molecules 1 have to be completely saturated by the RF pulse:

$$\left(\frac{M_0^* - M_s}{M_s}\right) = k_{CA}[CA]n_{ex}T_{1W} \quad (2)$$

For the specific case of fluorine containing compounds, the following applies for the fluorine or $^{19}$F signal:

$$M_F(t) = e^{-t/T2}M_F(0) = e^{-t/T2}k_{cal}[F] \quad (3)$$

where $k_{cal}$ is a calibration factor that relates the measured signal intensity $M_F(0)$ to the concentration of fluorine atoms [F]. This calibration factor depends on the imaging or spectroscopy scanning method and can be calibrated accurately. Furthermore, $k_{cal}$ is a function of $T_1$ (spin-lattice relaxation time), $T_2$ (relaxation time in transversal plane), TR (repetition time of RF pulse), TE (echo time).

Since for a given contrast agent the particle size and thus, in the example given, the number of fluorine atoms in one particle 2 are known the equation can be written as:

$$M_F(t)=e^{-t/T2}k_{cal}n_F[CA] \qquad (4)$$

where $n_F$ is the number of fluorine atoms per unit contrast agent (nanoparticle). The $^{19}$F images or spectra will generally be recorded with the shortest possible TE in order to have minimum signal loss. In that case the equation can in first approximation be written as $$M_F(0)=k_{cal}n_F[CA] \qquad (5)$$

Combined with eq. (2) this becomes:

$$\frac{\left(\frac{M_0^* - M_s}{M_s}\right)}{M_f(0)} = \frac{k_{CA}n_{ex}T_{1W}}{k_{cal}n_F} \qquad (6)$$

in which the concentration of the contrast agent has been eliminated. To obtain a correct pH map, the $T_{1W}$ can be obtained from other data, or if the hydrogen images are so-called proton density maps, this parameter term can be ignored because in proton density imaging the contrast is only determined by the number of hydrogen molecules and does not depend on either $T_1$ or $T_2$.

Compared to existing methods a main advantage of the method according to the present invention is that fewer images have to be combined in order to generate for example a concentration-independent pH map. As a consequence, the signal-to-noise ratio (SNR) of the pH map as determined by the method according to the present invention is improved with respect to prior art methods. In the method according to the present invention only ($M_{+2000}-M_{-2000}$) and calibration with the signal image from the non-responsive contrast entity, e.g. fluorine or $^{19}$F image, are required, i.e. only three images are required instead of four images in prior art methods. Therefore, the method according to the present invention will be easier to apply in clinical routine since it will be faster and less sensitive to motion or flow artefacts.

For example, the method described in international application with application number PCT/IB2006/051237 eliminates the concentration according to the following formula:

$$\frac{[(M_0^* - M_s)/M_s]^{freq2}}{[(M_0^* - M_s)/M_s]^{freq1}} = \frac{X^{freq2}}{X^{freq1}} \qquad (7)$$

With this method, five successive arithmetic steps have to be used, i.e. subtraction, division, subtraction, division and again division (see eq. (7)). Each step will increase the noise by a factor of the square root of 2. In the method according to the present invention only three successive arithmetic steps are needed, i.e. subtraction, division and again division (see eq. (6)).

Finally, the fact that the non-responsive contrast enhancing entity, e.g. $^{19}$F, is a non-native or exogenous marker gives the method a high degree of specificity. It eliminates the risk that image artefacts caused by motion or flow are mistaken as a CEST effect.

FIG. 3 schematically shows the cross-section of a device according to an embodiment of the present invention. In the middle of the scheme, a human body 11 is represented with a particular location 12 where a contrast agent according to the invention is located. At the bottom and at the top of the picture, cross-sections of four different elements are represented. The element 13 represented at the bottom-most and at the upper-most part of the drawing is a magnet of a classical MRI system. The second element 14 next to the magnet 13 is a gradient coil of a classical MRI system. The third element 15 next to the gradient coil 14 is the radio-frequency coil of a classical MRI system. This radio-frequency coil 15 is adapted to emit and receive radio-frequency waves such as 16 and 17, the radio-frequency waves 16 and 17 being suitable for exciting the responsive contrast enhancing entity and, hence in the case of a CEST contrast agent, is suitable for operating at the $^1$H frequency. The fourth element 18, which is here represented the closest to the body 11, is adapted to emit and receive radio-frequency waves such as 19, 20 and 21, the radio-frequency waves 19, 20 and 21 being suitable for exciting the non-responsive contrast enhancing entity and, hence, in case the non-responsive contrast agent comprises a fluorine containing compound, suitable for operating at the $^{19}$F frequency. On the right of the scheme, a controller 22 is represented connected to the gradient coil 14, the radio-frequency coil 15 and the multi-channel radio-frequency coil 18. The arrow 16 represents radio-frequency waves emitted from the radio-frequency coil 15 to the particular location 12 and the arrow 17 represents the modified signal coming back from the particular location 12. Once this signal 17 has been received by the radio-frequency coil 15, it is sent to the controller 22 where it will be analyzed in accordance with the methods of the present invention described above. The controller 22 may be configured as a computing device, e.g. comprising one or more workstations or personal computers or may be a dedicated processing engine.

Furthermore, the present invention includes a computer program product which provides the functionality of any of the methods according to the present invention when executed on a computing device. Further, the present invention includes a data carrier such as a CD-ROM or a diskette which stores the computer product in a machine readable form and which executes at least one of the methods of the invention when executed on a computing device. Nowadays, such software is often offered on the Internet or a company Intranet for download, hence the present invention includes transmitting the computer product according to the present invention over a local or wide area network. The computing device may include one of a microprocessor and an FPGA.

It is to be understood that although preferred embodiments, specific constructions and configurations, as well as materials, have been discussed herein for devices according to the present invention, various changes or modifications in form and detail may be made without departing from the scope and spirit of this invention.

For example, pH mapping can also be done with a contrast agent with a pH dependent relaxivity instead of a CEST contrast agent. Also in this case the signal is dependent on the pH as well as on the concentration of the contrast agent, which may be difficult to eliminate.

On the other hand, CEST can also be used for mapping of other parameters than pH such as, for example, temperature, $pO_2$ or metabolite concentration.

The invention claimed is:
1. A method for obtaining information concerning a physicochemical parameter by MRI imaging, the method comprising:
administering a contrast agent to a patient, the contrast agent comprising at least one non-responsive contrast enhancing entity giving a first signal, and at least one responsive contrast enhancing entity giving a second signal, the first signal being distinguishable from the second signal, acquiring MR images of at least a part of a body of a patient comprising the at least one responsive contrast enhancing entity, acquiring a calibration image in response to the first signal from the non-responsive contrast enhancing entity, and determining a value of the physicochemical parameter from the MR images and the calibration image, whereby the calibration image is used to compensate the value of the physicochemical parameter for the dependence of the MR images on the concentration of the contrast agent.

2. The method according to claim 1, wherein acquiring the calibration image includes:

determining the concentration of said non-responsive contrast enhancing entity from said calibration image, and using said determined concentration for reduction or elimination of contrast agent concentration dependency of the physicochemical parameter.

3. The method according to claim 1, further comprising:

determining a ratio of a first signal intensity used to generate an MR image and an intensity of the second signal used to generate the calibration image and deriving from this ratio the value of the physicochemical parameter.

4. A method according to claim 1, wherein the contrast agent comprises the non-responsive contrast enhancing entity attached to the at least one responsive contrast enhancing entity.

5. A method according to claim 4, wherein the at least one responsive contrast enhancing entity is covalently bound to the non-responsive contrast enhancing entity.

6. A method according to claim 1, wherein the contrast agent comprises a mixture of at least one non-responsive contrast enhancing entity and at least one responsive contrast enhancing entity.

7. A method according to claim 1, wherein the at least one non-responsive contrast enhancing entity has an MR resonance frequency different from the proton-resonance frequency of water.

8. A method according to claim 1, wherein the responsive contrast-enhancing entity is responsive to an RF pulse and is responsive to any of a change in pH, concentration, temperature or a combination there of.

9. A method according to claim 1, wherein the at least one non-responsive contrast enhancing entity is non-native to a human body.

10. A method according to claim 1, wherein the at least one responsive contrast enhancing entity is a CEST contrast agent molecule.

11. The method according to claim 1, the step of acquiring MR images including:

acquiring a reference MRI image of at least a part of a body of a patient comprising the at least one CEST contrast agent molecule and, acquiring a contrast enhanced MRI image of at least the part of the body of the patient comprising the at least one CEST contrast agent molecule, and determining the CEST effect in the part of the body from a comparison between the contrast enhanced MRI image and the reference MRI image.

12. A method according to claim 1, wherein the non-responsive contrast enhancing entity comprises a non-native MRI-active nucleus.

13. A method according to claim 12, wherein said non-responsive contrast enhancing entity is a fluorine containing compound.

14. A method according to claim 13, wherein the fluorine containing compound comprises a perfluorocarbon core and a lipid shell.

15. A method according to claim 13, wherein the fluorine containing compound comprises a polymer shell filled with a perfluoro-compound.

16. A method according to claim 1, wherein the non-responsive contrast enhancing entity comprises a polymer shell filled with a compound or mixture of compounds that have proton resonance frequencies different from the resonance frequency of water.

17. A method according to claim 10, wherein acquiring a reference MRI image of at least a part of a body of a patient is performed by irradiation of the CEST contrast agent molecule at symmetrical off-resonance frequency and wherein acquiring a contrast enhanced MRI image of at least the part of the body of the patient is performed by irradiation at exchangeable proton frequency of the CEST contrast agent molecule.

18. A method according to claim 10, wherein the CEST contrast agent molecule comprises at least one CEST-active paramagnetic complex, said at least one CEST-active paramagnetic complex comprising at least one exchangeable entity for enabling CEST.

19. A method according to claim 18, wherein the paramagnetic complex is a Yb-DOTAM derivative.

20. A method according to claim 1, wherein the physicochemical parameter is pH.

21. A non-transitory computer program product which, when executed on a processing device, performs or controls the method according to claim 1.

22. A machine-readable data storage device storing the non-transitory computer program product of claim 21.

* * * * *